United States Patent [19]

von Berg

[11] Patent Number: 5,237,999
[45] Date of Patent: Aug. 24, 1993

[54] DAMPER FOR PRESSURE MEASURING SYSTEMS

[75] Inventor: Peter von Berg, Neukeferloh, Fed. Rep. of Germany

[73] Assignee: Peter Von Berg Extrakorporale Systeme Medizintechnik GmbH, Kircheseeon/Eglharting, Fed. Rep. of Germany

[21] Appl. No.: 694,073

[22] Filed: May 1, 1991

[30] Foreign Application Priority Data

May 7, 1990 [DE] Fed. Rep. of Germany ....... 4014591

[51] Int. Cl.$^5$ .............................................. A61B 5/02
[52] U.S. Cl. ................... 128/673; 128/748; 73/753
[58] Field of Search ............. 73/707, 753, 715; 137/269; 251/118; 128/672, 34, 748, 5

[56] References Cited

U.S. PATENT DOCUMENTS

| 3,665,948 | 5/1972 | Hohberger | 73/707 |
| 3,865,100 | 2/1975 | Kanai et al. | 73/707 |
| 4,431,009 | 2/1984 | Marino, Jr. et al. | 128/674 |
| 4,517,844 | 5/1985 | Powell | 73/707 |
| 4,779,625 | 10/1988 | Cole . | |
| 5,143,077 | 9/1992 | Kobayashi | 128/685 |

FOREIGN PATENT DOCUMENTS 0328105 8/1989 European Pat. Off. .

Primary Examiner—Lee S. Cohen
Assistant Examiner—Robert L. Nasser, Jr.
Attorney, Agent, or Firm—Cushman, Darby & Cushman

[57] ABSTRACT

The damper for pressure measuring systems is integrated in the body (5) or insert of a valve. Flow passages (6, 7) communicate with a compartment (9) which is sealed by a rubber-elastic diaphragm (10). The side of the diaphragm remote from said compartment (9) defines a second compartment (13) which is connected to atmosphere through a port (14) designed to provide flow resistance.

4 Claims, 3 Drawing Sheets

DAMPER FOR PRESSURE MEASURING SYSTEMS

FIELD OF THE INVENTION

The invention relates to a damper for pressure measuring systems, for monitoring the pressure in blood pressure measurements comprising a flow passage and a compartment in fluid communication with said passage.

For the continuous monitoring of arterial blood pressure, a pressure measuring system is often used which consists of a catheter introduced into a peripheral artery, a transmission line filled with a liquid, and a pressure sensor which converts the pressure at the end of the transmission line into a proportional electrical signal. This signal is then indicated on a screen or evaluated in some other manner.

The transmission of dynamically varying pressures in closed liquid circuits creates the problem of reflections occurring from the maladaption of the pressure sensor to the liquid column; these reflections distort the measurement. For example, a pressure wave propagated from the patient to the pressure sensor is not fully absorbed by the pressure sensor but instead partly reflected by the sensor and return at reduced amplitude towards the patient. At the patient, the reflection will again be reflected back towards the sensor due to maladaptation. These multireflected pressure waves give rise to heterodyne waves whose resonant frequency may lie near a lower order harmonic of the first harmonic oscillation or the first harmonic. This may entail significant distortion of the measurement signal which cannot be removed from the evaluation.

BACKGROUND OF THE INVENTION

It is known (U.S. Pat. Nos. 4,431,009 and 4,335,729) that the parasitic oscillations can be attenuated by providing dampers in the vicinity of the pressure sensor in parallel with the transmission line. The dampers absorb part of the high frequency components of the pressure signal thereby moderating the amplitude of the reflected oscillations.

The damper, according to U.S. Pat. No. 4,431,009, is embodied in an adjustable needle valve which represents a flow resistance that can be varied. The damper is arranged as a separate aggregate between the pressure measuring transformer and a three-way valve. This valve links the transmission line between the patient and the pressure sensor to an infusion means because in the majority of cases when blood pressure is continuously measured the transmission line is rinsed with an infusion solution. Finally, a check valve is also located in the transmission line so it can cut off the pressure sensor from the measuring system. This is required to adjust the pressure sensor to atmospheric pressure.

The damper, according to U.S. Pat. No. 4,335,729 is likewise designed as a needle valve and is connected to a branch-off from the transmission line. It includes a sealed compartment totally surrounded by rigid walls and containing an air cushion to dampen the oscillations. The flow cross section of the connection between the transmission line and the compartment is regulated by the adjustable needle valve.

These dampers serve their purpose, however they are rather expensive for disposable items. Moreover, the additional adjustable component makes both measuring systems complex because they need to be continually adjusted. Finally, their structural design require the dampers to be mounted only at a certain distance from the pressure transducer so that their effect is not optimal.

German patent DE 24 05 584 responds to the problem of reflections in a system for the pulse-wise ejection of droplets by suppressing the reflected pressure wave with acoustic impedance matching through an elastic conduit.

German patent DE 29 41 118 shown a liquid spring damper comprising of two pot-like compartments which are supported "floatingly" with respect to each other by a shear spring. The two compartments communicate through a throttle. An elastic bellow is arranged inside the inner compartment and, as it is pressurized by adjustable gas pressure, it blocks the throttle at an appropriate gas pressure. The throttle does not open until the pressure n the main compartment exceeds that in the bellows. In this manner, a damper is provided which has a nonlinear characteristic and is adjustable by the pressure inside the bellows.

SUMMARY OF THE INVENTION

It is the object of the invention to improve the damper of the kind mentioned above so that it will have a more compact structure.

The present had the damper integrated in a valve insert or body of the valve. The flow passage through the valve insert communicates through a capillary bore with a compartment formed in the valve insert and closed off by a rubber-elastic diaphragm. The diaphragm is supported so that it can be deformed primarily only in the direction that enlarges the compartment. There is another compartment on the other side of the diaphragm remote from the first compartment. This second compartment is connected to the atmosphere through a nozzle or port thereby communicating with ambient pressure. The diameter of the second compartment is bigger than the first so that the diaphragm can be deformed in the desired direction only.

According to another variant of the invention, the movability of the diaphragm is limited, or even prevented altogether, by introducing a plunger into the second compartment. When it is in its one limited position, the plunger comes into contact with the diaphragm on its face end, and thereby blocks diaphragm movements. When the plunger is in any intermediate position, the maximum amplitude of deflection of the diaphragm will be limited and the volume of the second compartment will be varied.

The damper is preferably integrated in the valve insert of a three-way valve. However, it may also e integrated in other types of valves, such as a simple shutoff valve according to a modification of the invention.

BRIEF DESCRIPTION OF THE DRAWING

The invention will be described further, by way of example, with reference to the accompanying drawings, in which.

DESCRIPTION OF THE PREFERRED EMBODIMENTS

Figure 1:
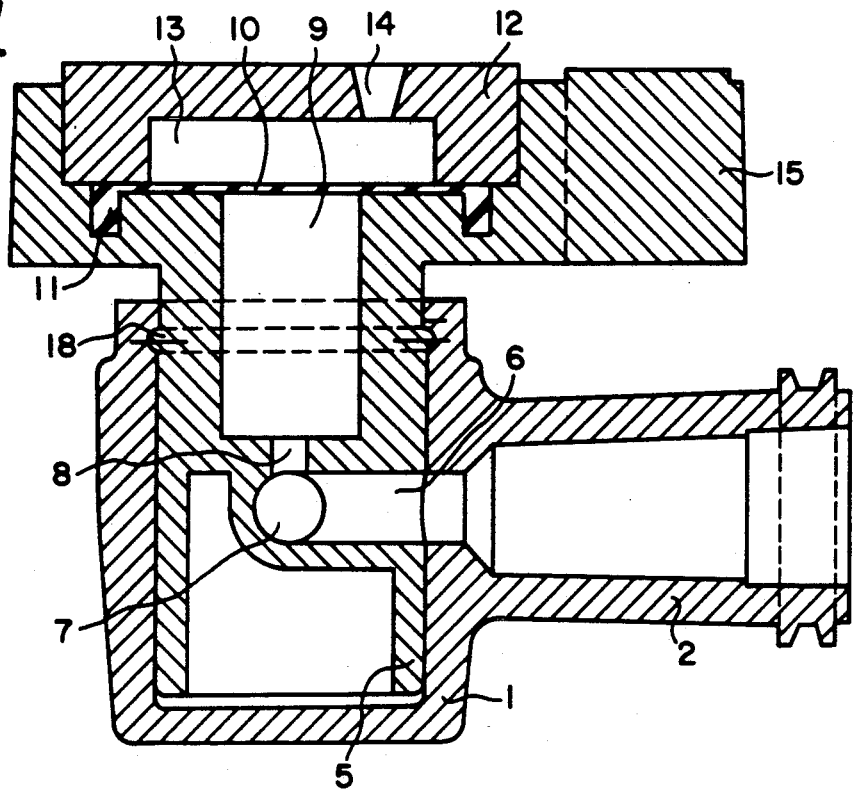
FIG. 1 is a cross sectional view of the damper in the valve insert of a three-way valve according to a first embodiment of the invention.

The three-way valve shown in FIG. 1 comprises a casing 1 which has three connecting ends 2, 3, 4 (cf. FIGS. 3 and 4) and in which a valve insert 5 (plug) is received. Depending on the rotary position of the valve insert passages 6 and to establish the valve insert flow connection between the various connecting ends 2, 3, and 4. In this respect, the valve is a conventional three-way valve.

A damper is integrated in the vale insert 5. To achieve this, passages 6 and 7 in valve insert 5 are in fluid communication through a capillary bore 8 with a first compartment 9. The first compartment is integrated in the valve insert and in the embodiment shown is of cylindrical shape. The face end of the first compartment 9 remote from the capillary bore 8 is closed by a rubber-elastic diaphragm 10. The rim of the diaphragm 10 is retained in an annular groove 11 presented in a widening handle 15 of the valve insert. The diameter of the diaphragm 10 is distinctly greater than the diameter of the cylindrical first compartment 9 so that considerable portions of the diaphragm edge lie on the face end of the wall which defines the first compartment 9. In this manner, the diaphragm 10 can be deform to a greater extend in the direction of enlarging the first compartment 9 than in the opposite direction.

The diaphragm 10 is retained by a cover 12 which is U-shaped in cross section and inserted in a recess formed in the handle 15. The shape of cover 12 together with the diaphragm 10 forms a second compartment 13. The diameter of the second compartment 13 is greater than that of the first compartment 9.

The cover 12 has a nozzle-like port 14 through which ambient or atmospheric pressure is admitted to the second compartment 13. The dimension of the port 14 is chosen so small that it presents flow resistance to the air which is exchanged between the compartment 13 and the surroundings upon deflection of the diaphragm.

Figure 2:
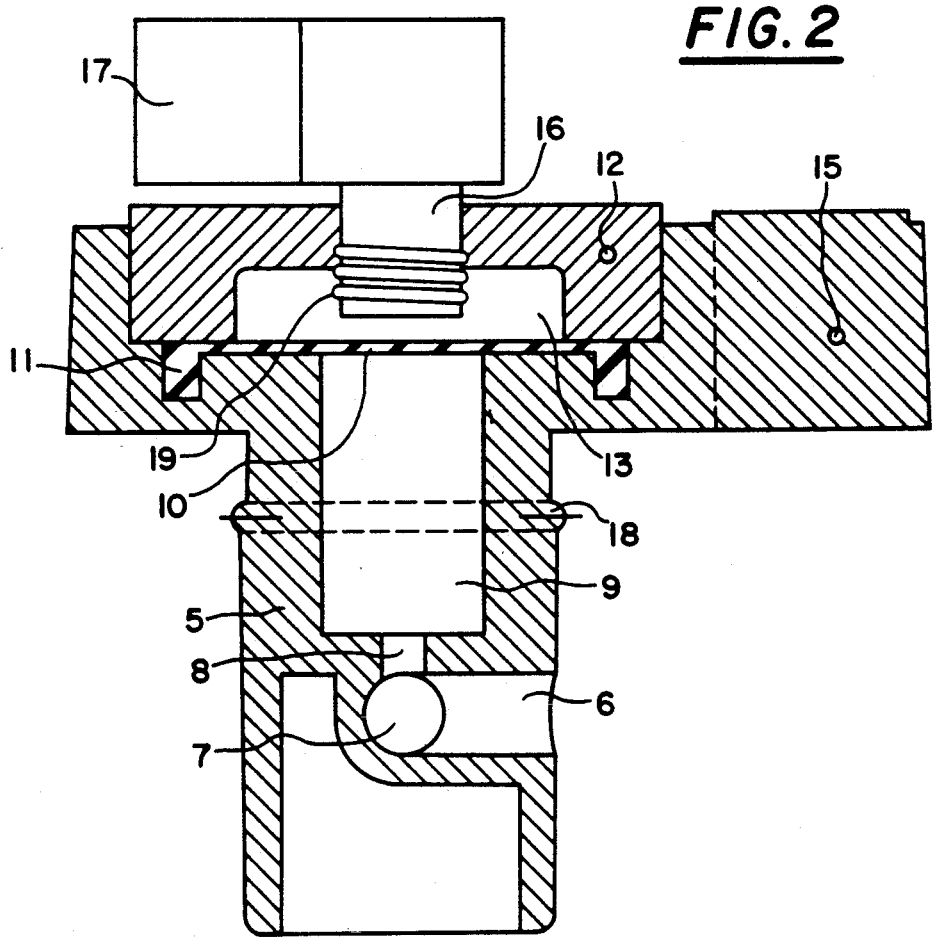
FIG. 2 is a cross sectional view of a valve insert with damper according to a second embodiment of the invention.

In the embodiment illustrated in FIG. 2, the damper is adapted to be switched by a plunger 16. The plunger 16 is placed in the cover 12 and can be displaced in the axial direction. When the plunger is in one limited position it will contact the diaphragm, thereby preventing the diaphragm from oscillating. The diameter of the plunger corresponds approximately to the diameter of the first compartment 9, so that when it is in the limit position the face end of the plunger fully covers that area of the diaphragm 10 which closes the first compartment 9. In the embodiment shown, this plunger is threaded into the cover 12 by means of a thread 19 of relatively great pitch. A lever 17 is provided for actuation of the plunger 16. As an alternative, a vertical-horizontal lever an eccentric may be provided to selectively prevent deflections of the diaphragm. As the thread between the plunger 16 and the cover 12 is not absolutely tight, the function served by the port 14 in the embodiment according to FIG. 1 is fulfilled at the same time.

Figure 3:
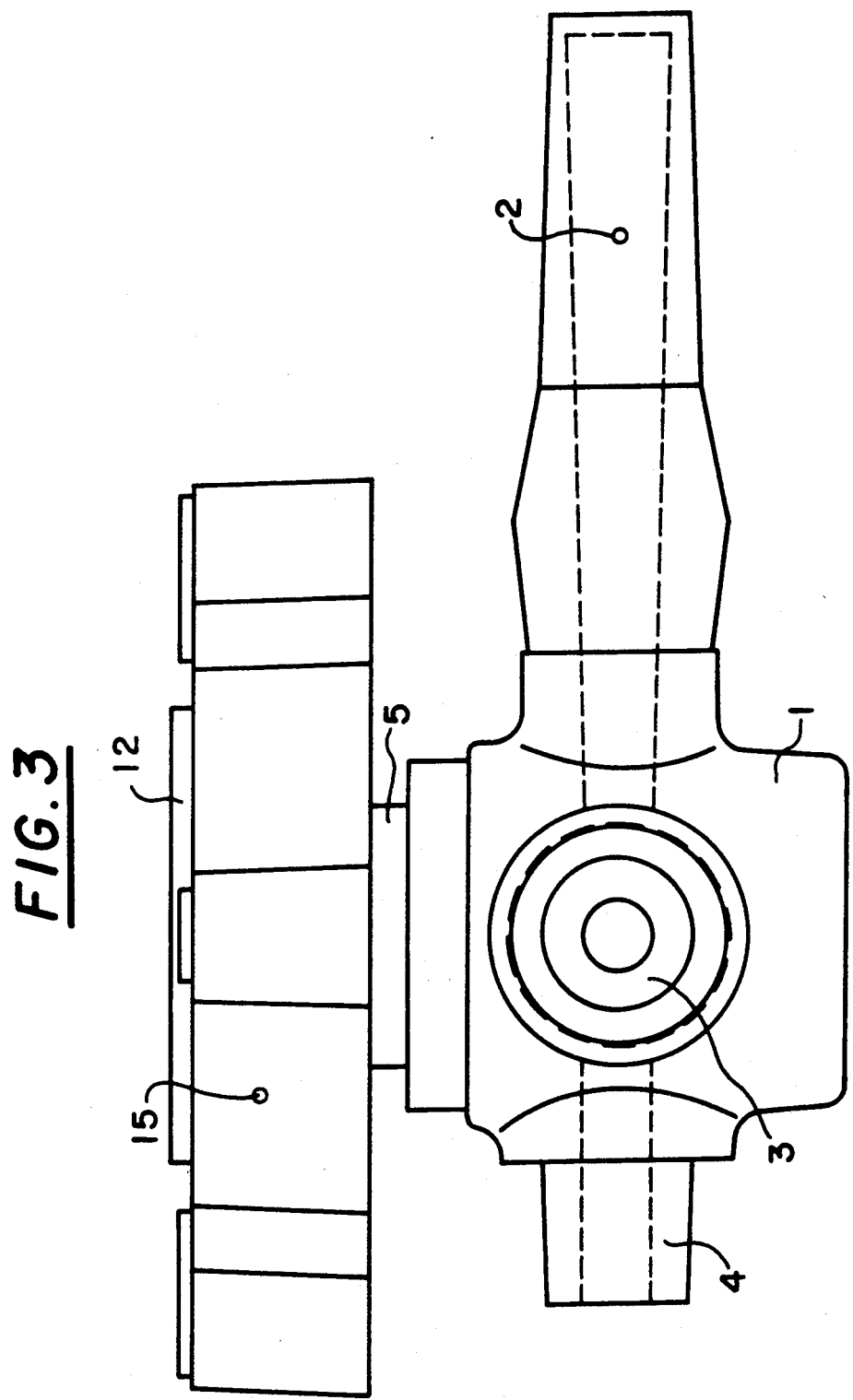
FIG. 3 is a side elevational view of a three-way valve including an integrated damper.
Figure 4:
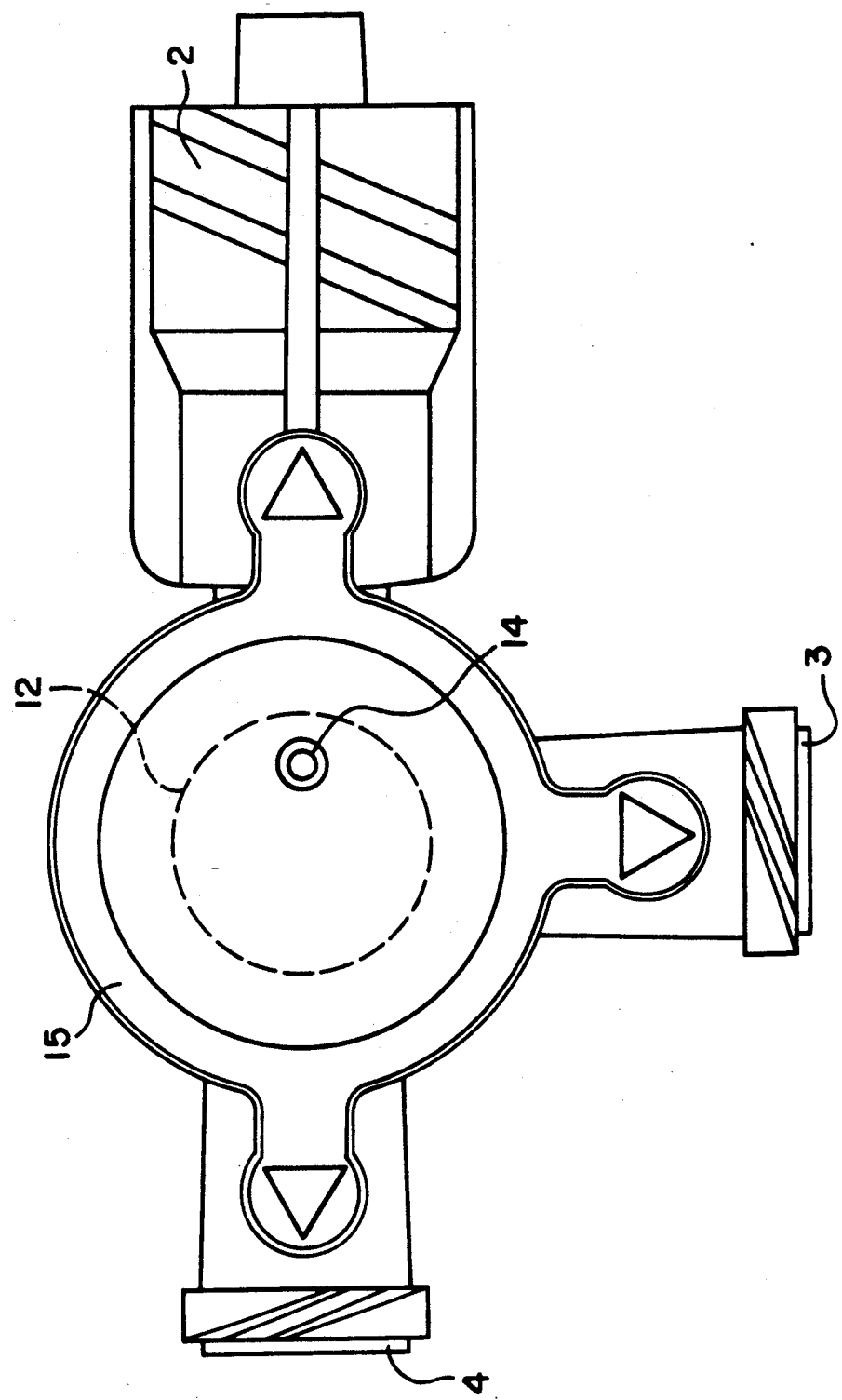
FIG. 4 is a top plan view of the valve shown in FIG. 3.

FIGS. 3 and 4 are presentations of a three-way valve with an integrated damper.

The valve with its damper may be secured by way of flanges directly to the measuring transformer (not shown) thereby offering a good damping characteristic throughout the measuring circuit. The collar 18 shown in FIGS. 1 and 2 at the valve insert serves to arrest the valve insert in the casing against any movement in axial direction.

What is claimed is:

1. A damper for a pressure measuring system, integrated into a valve body comprising:
   means for defining a flow passage;
   a first compartment in fluid communication with said flow passage;
   a rubber elastic diaphragm sealing said first compartment;
   a second compartment sealed from said first compartment by said diaphragm; and
   switchable locking means for selectively blocking deflections of said diaphragm.

2. The damper as claimed in claim 1,
   wherein said locking means includes a plunger adapted to be threaded into a cover of said valve by way of a thread which serves as a nozzle-like port and connects said second compartment to atmospheric pressure.

3. The damper as claimed in claim 2, wherein the damper is integrated in the valve body of a three-way valve.

4. The damper as claimed in claim 2, wherein the damper is integrated in the valve body of a shutoff valve.

* * * * *